(12) United States Patent
Zhu et al.

(10) Patent No.: US 6,192,275 B1
(45) Date of Patent: Feb. 20, 2001

(54) ADAPTIVE EVOKED RESPONSE SENSING FOR AUTOMATIC CAPTURE VERIFICATION

(75) Inventors: Qingsheng Zhu, Little Canada; Mark Gryzwa, Woodbury; Geng Zhang, Vadnais Heights; Arthur Olive, Stacy, all of MN (US)

(73) Assignee: Cardiac Pacemakers, Inc., St. Paul, MN (US)

( * ) Notice: Under 35 U.S.C. 154(b), the term of this patent shall be extended for 0 days.

(21) Appl. No.: 09/309,925

(22) Filed: May 11, 1999

(51) Int. Cl.[7] ................................................. A61N 1/362
(52) U.S. Cl. ............................................................. 607/28
(58) Field of Search ................................... 607/27, 28, 9, 607/5

(56) References Cited

U.S. PATENT DOCUMENTS

| | | |
|---|---|---|
| 5,324,310 | 6/1994 | Greeninger et al. ................... 607/28 |
| 5,350,410 | 9/1994 | Kleks et al. ............................ 607/28 |
| 5,683,431 | 11/1997 | Wang ..................................... 607/28 |

*Primary Examiner*—Scott M. Getzow
(74) *Attorney, Agent, or Firm*—Nikolai, Mersereau & Dietz, P.A.

(57) ABSTRACT

An implantable cardiac rhythm management device adapted to receive and digitize electrocardiogram signals from leads placed on or in the heart and capable of automatically adjusting an evoked response detection threshold dependent upon a modulation of the amplitude of the evoked response. Respiration, activity level, and lead maturation, among others, all effect the modulation of the evoked response and the amplitude of a signal associated with evoked response. The present invention automatically adjusts the evoked response detection threshold to account for this modulation. Without limitation, the automatic adjustment of the evoked response detection threshold may be utilized during an automatic capture verification sequence. In the event of non-capture or fusion beats during an automatic adjustment, the evoked response detection threshold is not adjusted.

16 Claims, 6 Drawing Sheets

ADAPTIVE EVOKED RESPONSE SENSING FOR AUTOMATIC CAPTURE VERIFICATION

BACKGROUND OF THE INVENTION

I. Field of the Invention

This invention relates generally to a device for stimulating cardiac tissue, and more particularly relates to an implantable cardiac rhythm management device and method for automatically adjusting the evoked response detection threshold. Without limitation, during automatic capture verification the cardiac rhythm management device receives and digitizes an electrocardiogram signal of the patient's heart and adjusts the evoked response detection threshold dependant upon modulation or changes in the amplitude of the evoked response from beat-to-beat. Several factors influence the modulation of the amplitude associated with the evoked response including respiration of the patient. The respiration of the patient affects the amplitude of the evoked response for each R-wave, increasing and decreasing the amplitude in a cyclic fashion. Other factors further modulate the amplitude of the evoked response for each R-wave. The present invention accordingly adjusts the evoked response detection threshold in relation to the modulation of the amplitude of the evoked response.

II. Discussion of the Prior Art

For the most part, prior art implantable cardiac rhythm management devices, including bradycardia and tachycardia pacemakers and cardiac defibrillators, have sense amplifier circuits for amplifying and filtering electrogram signals detected by electrodes placed in or on the heart and which are coupled by suitable leads to the implantable cardiac rhythm management device. Typically, the signals emanating from the sense amplifier are applied to one input of a comparator circuit whose other input is connected to a source or reference potential. Only when an electrogram signal from the sense amplifier exceeds the preprogrammed reference potential threshold will it be treated as a cardiac paced or sensed beat. The source reference potential may be referred to as an evoked response detection threshold.

Typically, the reference potential threshold is set at a fixed amount that is expected to exceed the maximum amplitude of artifact. If, however, the threshold is not set high enough, then artifact may result in malsensing. Further, if the reference potential threshold is set too high, then the amplitude associated with an R-wave may not be sufficient to trigger the reference potential threshold.

The inventors of the present invention have determined that several factors influence the amplitude associated with R-waves. For example, respiration of the patient fluctuates the amplitude of the evoked response in a cyclic fashion increasing and decreasing over several beats. This fluctuation makes it even less desirable for the reference potential threshold to be set at a fixed amount. Other factors, described in greater detail below, affect the amplitude of the evoked response. Thus, a need exists for a cardiac rhythm management device that automatically adjusts the evoked response detection threshold in conjunction with fluctuations in the amplitude associated with a particular R-wave, taking into account the modulation of the amplitude corresponding to the evoked response for each R-wave. The present invention meets these and other needs that will become apparent from a review of the description of the present invention.

SUMMARY OF THE INVENTION

The present invention provides a method and apparatus for automatically adjusting an evoked response sensing/detection threshold (ER threshold) in a cardiac rhythm management device, wherein the ER threshold is set dependant upon a determined modulation of the amplitude corresponding to evoked response R-wave. The automatic adjustment of the ER threshold in accordance with the present invention is particularly useful during an automatic capture verification pacing sequence. The rhythm management device of the present invention may include a sense amplifier for amplifying and filtering electrocardiogram signals detected by electrodes of a lead that is coupled to the sense amplifier. Also included is a power supply, peak detector, timing circuit, controller coupled to receive the sensed electrogram signals and means controlled by the controller for applying cardiac stimulation pulses to a patient's heart. The stimulation pulses are applied in response to control signals from the controller. The sense amplifier may include a 4–150 Hz wide-band pass filter.

The rhythm management device includes detecting means, means for determining a value associated with modulation and adjusting means each of which may be constructed of separate suitable components or may be internal to the controller. The controller may be in any of several forms including a dedicated state device or a microprocessor with code, and may include ROM memory for storing programs to be executed by the controller and RAM memory for storing operands used in carrying out the computations by the controller.

The controller and components contained therein or coupled thereto detect and distinguish cardiac depolarization deflections from the electrocardiogram signal. A peak detector, for example, is utilized to in affect determine the amplitudes of the cardiac depolarization deflections or evoked response. A value associated with modulation of the amplitude of the evoked response is determined from several cardiac depolarization deflections. The evoked response detection threshold is adjusted dependant upon the determined value associated with modulation.

In the preferred embodiment, during a mode of automatic capture verification the implantable cardiac rhythm management device is capable of automatically sensing an evoked response of a patient's heart and has an adjustable evoked response detection threshold. The cardiac rhythm management device includes a pulse generator, a controller that activates the pulse generator, conduction means for conducting an electrocardiogram signal including electrical impulses corresponding to a cardiac depolarization and noise, and detecting means coupled to the conduction means for detecting from the electrocardiogram signal an evoked response of the patient's heart. The detecting means includes an adjustable evoked response detection threshold, means for determining a value associated with modulation of the amplitude of the evoked response, and adjusting means for adjusting the detection threshold dependant upon a determined value associated with modulation.

The implantable cardiac rhythm management device may also include an evoked response filter means for determining an amount or value associated with a maximum amplitude of the detected evoked response over a predetermined number of beats and an amplitude of an immediately prior determined maximum amplitude of the detected evoked response. The adjusting means for adjusting the evoked response detection threshold may also adjust the threshold dependant upon the value associated with the evoked response filter means. Further, the adjusting means may incorporate a respiration modulation index that is determined from a measured mean maximum amplitude of the detected evoked response over a predetermined number of beats and a minimum maximum amplitude of the detected evoked response over the predetermined number of beats. Also, an amount associated with an evoked response minimum is determined by the controller from the determined respiration modulation index and an amount derived from the evoked response filter. Additionally, the implantable cardiac rhythm management device may include a means for determining an amount associated with an artifact baseline of the electrocardiogram signal, wherein the amplitude of the ER detection threshold is set greater than the amount associated with the maximum amplitude of the artifact baseline and less than an evoked response minimum.

In use, the cardiac rhythm management device includes a preset protocol for automatically adjusting the evoked response detection threshold utilizing the controller and associated components. The peak detector and controller, for example, may determine a maximum amplitude from an electrocardiogram signal corresponding to each evoked response for a predetermined number of heart beats. The predetermined number of heart beats may be patient dependent ranging from 6 to 18 beats or more, however twelve heart beats is preferred. The peak detector and/or comparator are utilized to determine the "maximum" amplitude of the electrocardiogram signal. Likewise, the peak detector and controller determine the "maximum" amplitude of artifact. The maximum amplitude of artifact is preferably determined during a step down pacing protocol when loss of capture occurs. Those skilled in the art will appreciate that a separate pacing stimulus of known sub-threshold output may be applied to thereafter measure the amplitude of artifact. The controller then determines either through calculation or other known suitable means, the mean of the "maximum" amplitudes from the electrocardiogram signal corresponding to each evoked response over the predetermined number of beats.

The controller or other suitable component also determines a maximum and minimum of the maximum amplitude from the electrocardiogram signal corresponding to each evoked response at a predetermined pacing output over the predetermined number of beats. Once the mean maximum amplitude and minimum maximum amplitude are determined, a constant value or respiration modulation index is determined as a function of the determined mean maximum amplitude and minimum maximum amplitude. Further, a value associated with the measured maximum amplitude of the evoked response and an immediately prior measured maximum amplitude is determined for a predetermined number of heart beats. Once these amounts are determined, then the evoked response detection threshold is set as a function of the measured modulation and the maximum amplitude of artifact. Without limitation, the evoked response detection threshold may be utilized during autocapture, for example, to help determine whether a pacing stimulus having a predetermined output evokes a response in the patient's heart. During autocapture, the electrocardiogram signal must have an amplitude exceeding the evoked response detection threshold before a conclusion is made that the pacing stimulus is "captured" or evokes a response.

In the preferred embodiment, the value associated with modulation is reset and re-determined once every 21 hours and the evoked response detection threshold is accordingly re-set. Those skilled in the art will appreciate that the evoked response detection threshold is not re-set if an evoked response is not detected. Further, if a fusion beat is detected then the evoked response detection threshold is not re-set.

OBJECTS

It is accordingly a principal object of the present invention to provide a rhythm management device that automatically adjusts the evoked response detection threshold on a beat by beat basis, such that the detection threshold is adjusted dependant upon the modulation of the evoked response amplitude and artifact.

Another object of the present invention is to provide a method of adjusting the evoked response detection threshold dependant upon modulation of the evoked response amplitude due to respiration modulation.

Still another object of the present invention is to provide a rhythm management device that adjusts the evoked response detection threshold during an automatic capture verification sequence.

These and other objects and advantages of the present invention will become readily apparent to those skilled in the art from a review of the following detailed description of the preferred embodiment especially when considered in conjunction with the claims and accompanying drawings in which like numerals in the several views refer to corresponding parts.

DESCRIPTION OF THE PREFERRED EMBODIMENT

The present invention represents broadly applicable improvements to an implantable cardiac rhythm management device capable of automatically adjusting an evoked response detection threshold for identifying an evoked response or R-wave of a patient's heart. The evoked response detection threshold is automatically adjusted as a function of detected modulation of the evoked response amplitude and artifact "measured" during a predetermined period. The embodiments detailed herein are intended to be taken as representative or exemplary of those in which the improvements of the invention may be incorporated and are not intended to be limiting.

Figure 1:
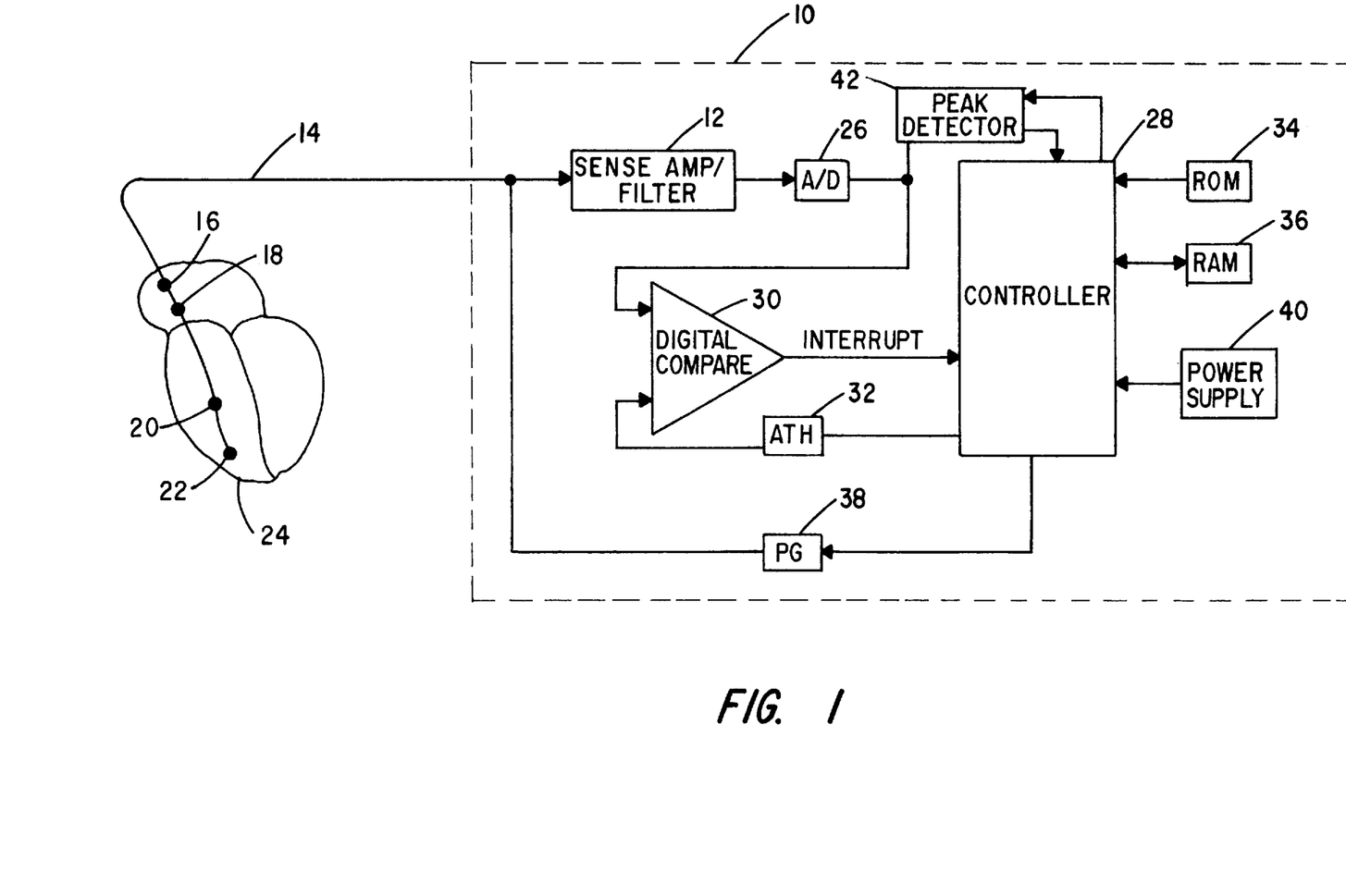
FIG. 1 is a general block diagram of a cardiac rhythm management device that may incorporate the automatic evoked response threshold adjustment of the present invention.

Referring first to FIG. 1, there is illustrated by means of a block diagram, a hardware platform in which the auto-adjust algorithm of the present invention may be utilized. Shown enclosed by the broken line box 10 is circuitry which may be included within a cardiac rhythm management device, such as a pacemaker. It is seen to include a sense amplifier/filter 12 having its input connected by a pacing lead 14. The pacing lead 14 is shown having a plurality of electrodes 16–22 coupled to lead 14 and disposed on or in the heart 24. An electrocardiogram signal is transmitted through the pacing lead 14 to the sense amplifier/filter 12.

In FIG. 1, the lead 14 is shown as a bipolar single pass VDD or DDD lead, various forms of which are known to those skilled in the art. Without limitation, the electrodes 20 and 22 are designed to detect ventricular depolarization while electrodes 16 and 18 sense atrial depolarization. The controller 28 is coupled to power supply 40 and provides a control output to a pulse generator 38 at appropriate times. The resulting pulses are applied over the lead 14 to the electrodes 16, 18, 20 and/or 22 for providing electrical stimulation to the heart 24. The arrangement shown in FIG. 1 can be used for sensing a response evoked by a pacing pulse in the ventricles.

The sense amp/filter circuit 12 conditions the electrogram signal and then applies the conditioned signal to an analog-to-digital converter 26 which converts the conditioned signal to corresponding digital values compatible with a peak detector 42. From the analog-to-digital converter 26, the signal is transmitted to both peak detector 42 and a comparator 30. Without any limitation intended, the peak detector may include a digital comparator and register, wherein the signal transmitted from the A/D converter 26 is continuously compared with an initial value stored in the peak detector register. If the current signal is greater than the value stored in the peak detector, the current value is loaded into the register value and is then stored in the peak detector register as a "maximum" amplitude. The peak detector 42 includes a clearing mechanism controlled by the controller 28. Those skilled in the art will recognize that timers, utilized to activate and deactivate the peak detector, may be either external or internal to the controller 28. Once the peak detector 42 times out, the final peak detector register value is transmitted to the controller 28. In this manner the peak detector 42 may be utilized to determine the amplitudes of the cardiac depolarization events.

The output from the A/D converter 26 may also be applied as a first input to a digital comparator 30. A second reference input is compared by digital comparator to the first input transmitted from the A/D converter 26. The reference input of the comparator 30 is a digital value stored in the ATH register 32. The controller 28 may periodically compute and modify the digital value stored in the ATH register 32. Without limitation, the reference input of the comparator 30 may correspond to, for example, the evoked response detection/sensing threshold. Of course, other components of suitable known construction are utilized to provide the operable cardiac rhythm management device of the present invention.

The drawing of FIG. 1 shows only one hardware configuration in which the algorithm of the present invention can be implemented. Those skilled in the art will appreciate that the circuit of FIG. 1 can be modified so that, for example, the digital comparator 30 and ATH register 32 can be internal to the controller 28. It is also possible to add an additional digital comparator in parallel with the digital comparator 30 and provide a separate threshold register for corresponding sensing threshold (ST) rather than time sharing the digital comparator 30 between the detection of cardiac depolarization and noise. The controller 28 may be in any of several forms including a dedicated state device or a microprocessor with code, and may include ROM memory 34 for storing programs to be executed by the controller 28 and RAM memory 36 for storing operands used in carrying out the computations by the controller 28.

Figure 2:
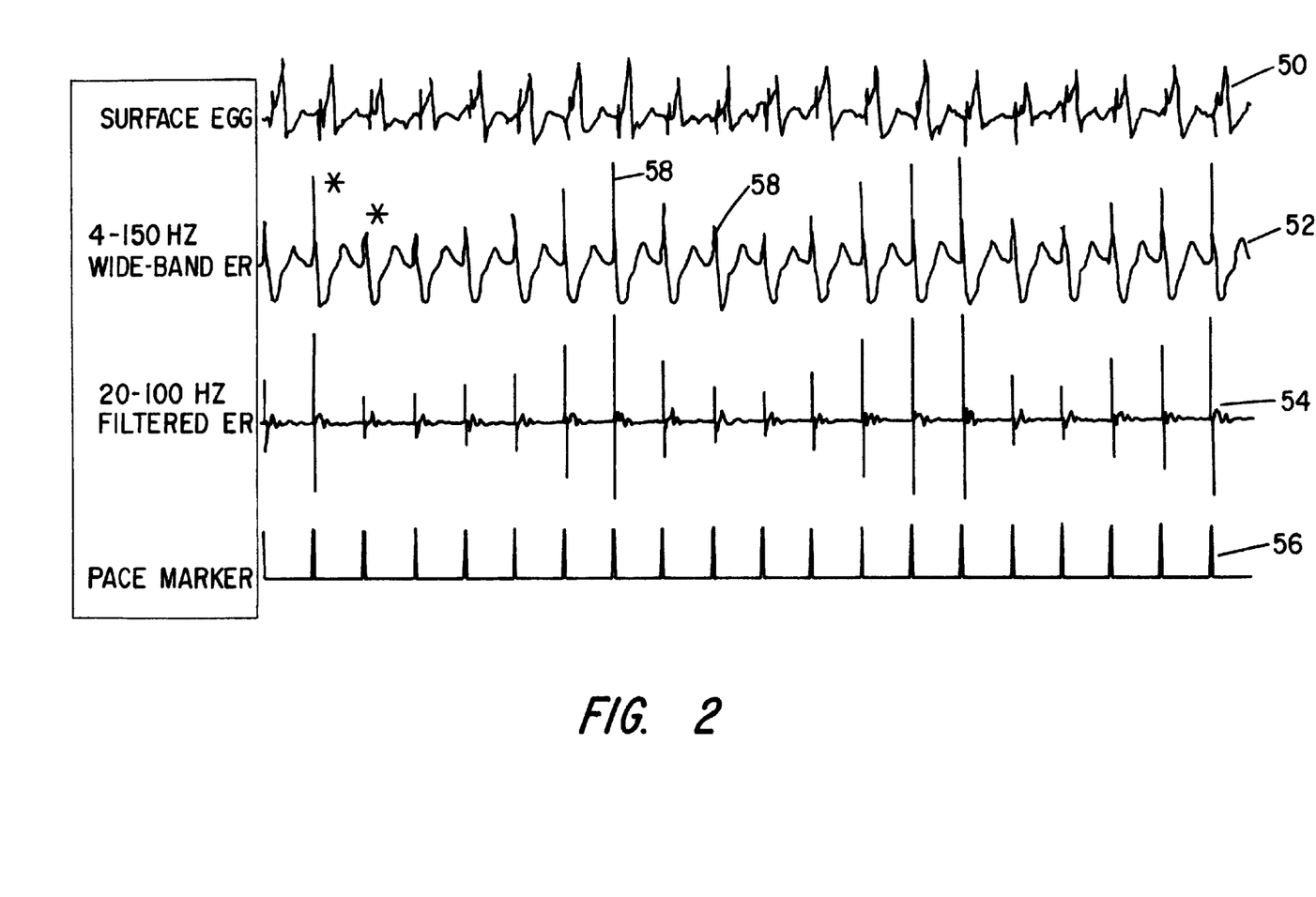
FIG. 2 is a graph of an electrogram and filtered signals shown in association with a pace marker, which together illustrates the modulation of the evoked response amplitude.

Referring to FIG. 2, there is shown a surface electrocardiogram signal 50, a corresponding first waveform 52 of the electrocardiogram signal filtered through a sense amplifier having a wide-band pass filter array, a corresponding second waveform 54 of the electrocardiogram signal filtered through a sense amplifier having a typical band pass filter array and the pacing event marker 56 associated with the resulting electrocardiogram signal. A cardiac depolarization or R-wave deflection 58 is pronounced in the filtered first and second waveforms 52 and 54. The inventors have observed that over several beats the amplitude of the R-wave fluctuates or modulates. Without limitation, the modulation has been found to result from factors such as activity level of the patient, variations in the pacing output voltage, respiration of the patient, administration of pharmaceutical agents, and lead maturation, among others. Modulation due to respiration has been observed as cyclic in nature. These cyclic fluctuations or respiration modulations have been observed in both bi-polar and uni-polar sensing configurations.

Figure 3:
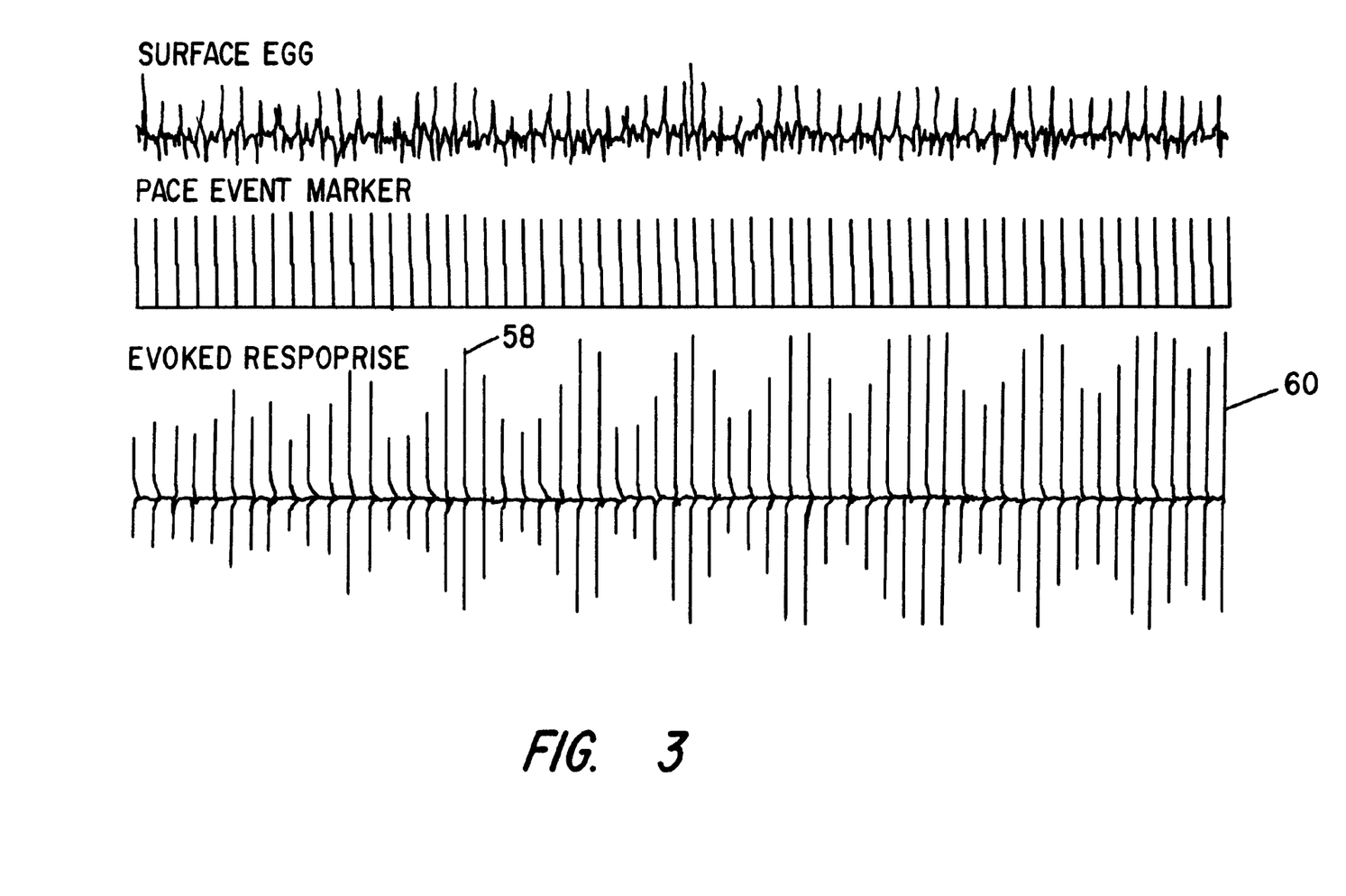
FIG. 3 is a graph of an electrogram and filtered signals shown in association with a pace marker, which together illustrates the modulation of the evoked response amplitude due to respiration modulation.
Figure 4:
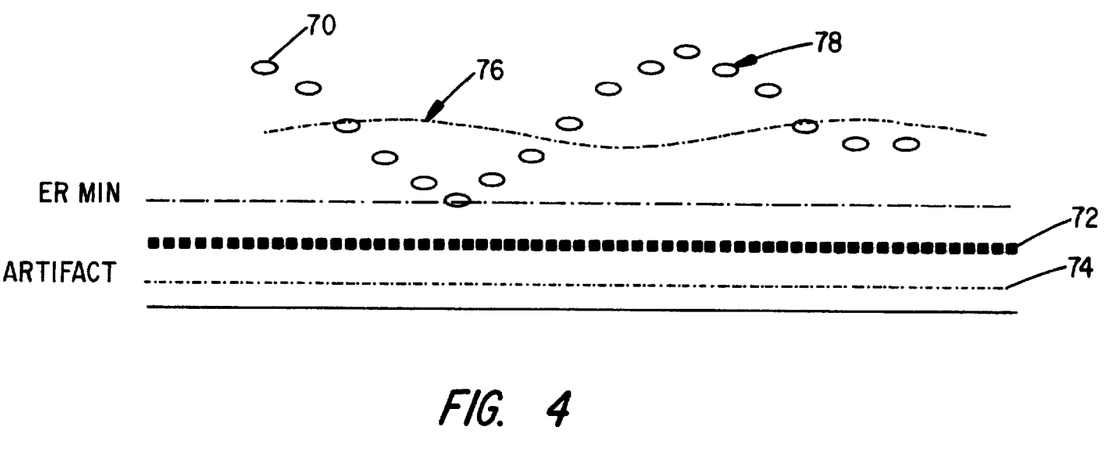
FIG. 4 is a graph of the amplitude of evoked response for several beats, shown relative to the evoked response minimum and evoked response filter.
Figure 5:
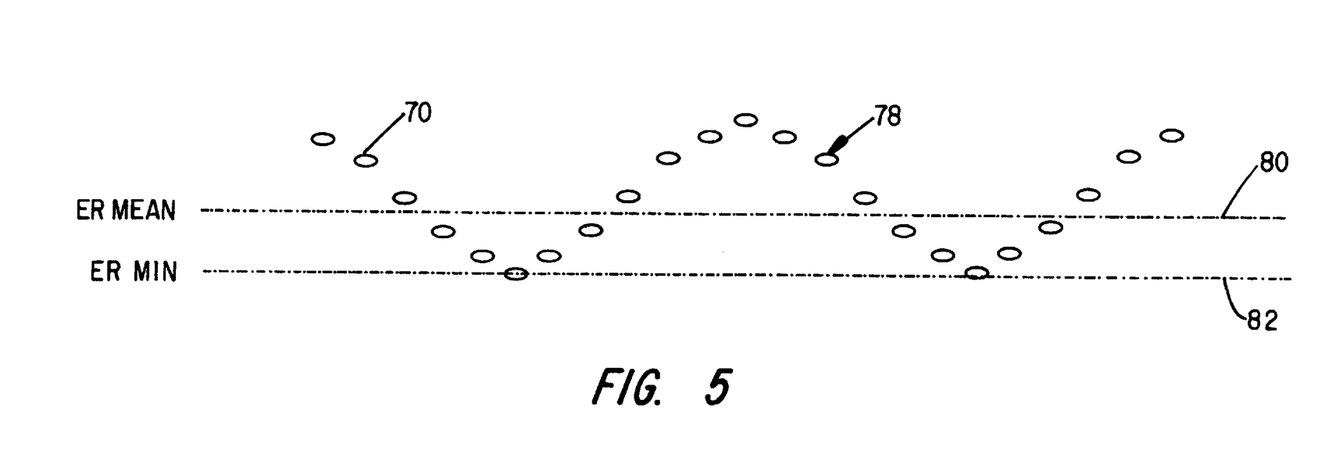
FIG. 5 is a graph of the amplitude of evoked response for several beats, shown relative to the evoked response minimum and evoked response mean.

Referring to FIG. 3, a case study is shown for exemplary purposes, wherein the amplitude of the R-wave 58 for the evoked response waveform 60 fluctuates over a cyclic pattern. The amplitude of each R-wave 58 can be seen to fluctuate over several beats wherein the amplitude of the R-wave having the greatest amplitude is more than twice the amplitude of the R-wave having the smallest amplitude. This modulation in R-wave amplitudes is significant when considering/setting the threshold amplitude that must be detected before an evoked response of the patient's heart is assumed. FIGS. 4 and 5 further illustrate the need to define an evoked response detection threshold sufficient to detect evoked response during an entire respiration modulation, without setting the threshold so low that detected artifacts exceeds the threshold.

Referring to FIG. 4, several points 70 are shown plotted relative to an evoked response detection threshold baseline 72, an artifact baseline 74, and an evoked response filter baseline 76. The resulting modulating waveform 78 is shown in relation to the threshold baseline 72. Each point 70 corresponds to a maximum amplitude for a corresponding evoked response. FIG. 5 shows the modulating waveform 78 in relation to the evoked response "mean" baseline 80 and the evoked response "minimum" baseline 82. The evoked response mean baseline 80 represents the mean of several maximum amplitudes of several R-waves over several beats. Likewise, the evoked response minimum baseline 82 represents the minimum amplitude of several maximum amplitudes of several R-waves over several beats.

Figure 6:
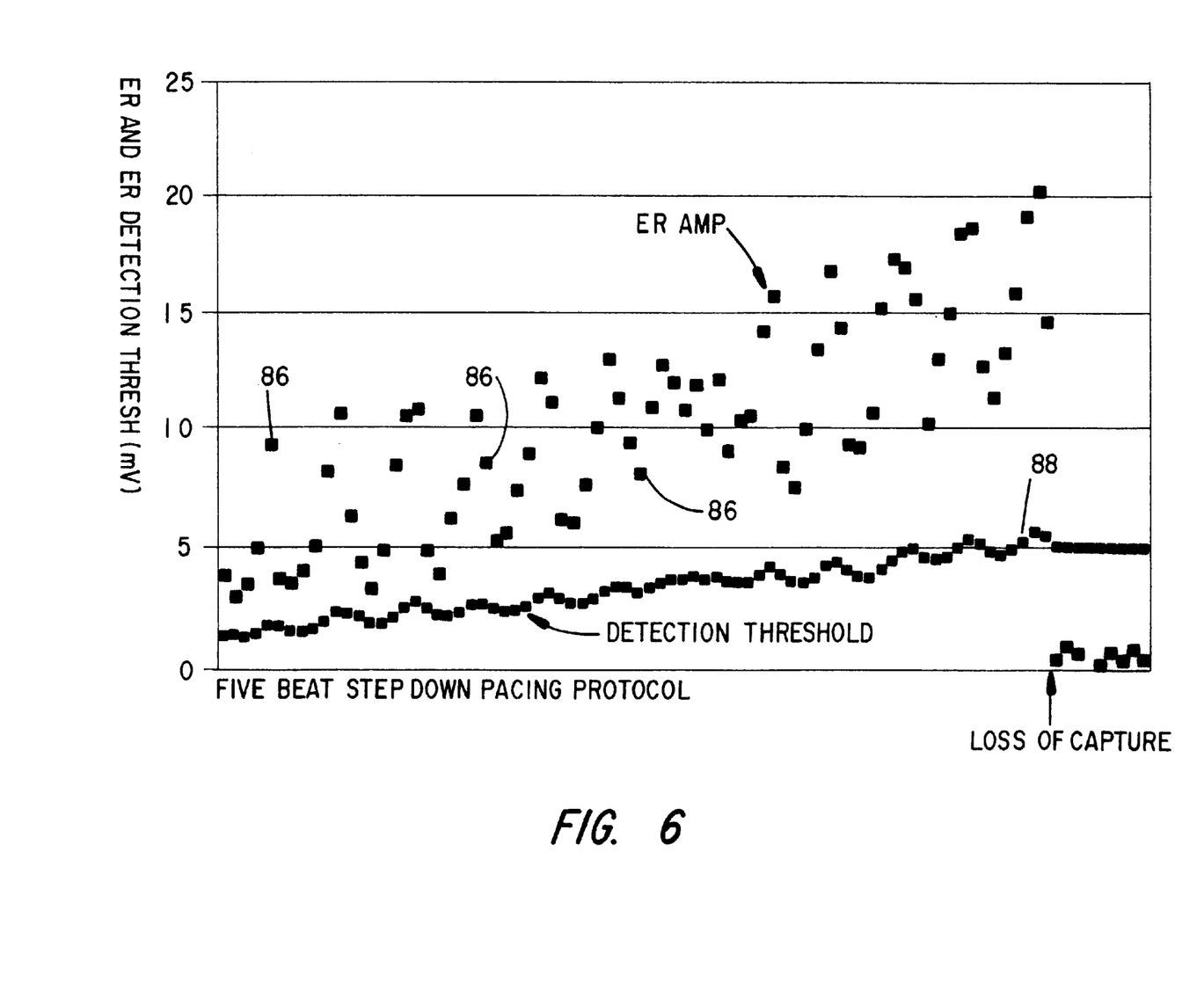
FIG. 6 is a graph of the amplitude of evoked response for several beats during a five-beat step down capture detection pacing protocol.

Referring now to FIG. 6, the maximum amplitude of several R-waves indicated at point 86 are shown measured over time, wherein the "measurements" of the amplitude occurred during a five-beat step down capture detection pacing protocol. The evoked response detection threshold baseline 88 as determined by the method of the present invention is shown, wherein fluctuation in the baseline coincides with the modulation of the evoked response amplitude. In this manner, during beat by beat autocapture, for example, a decrease in the evoked response amplitude is not likely to generate a false negative in capture decision making, thereby eliminating unnecessary backup pacing.

Figure 7:
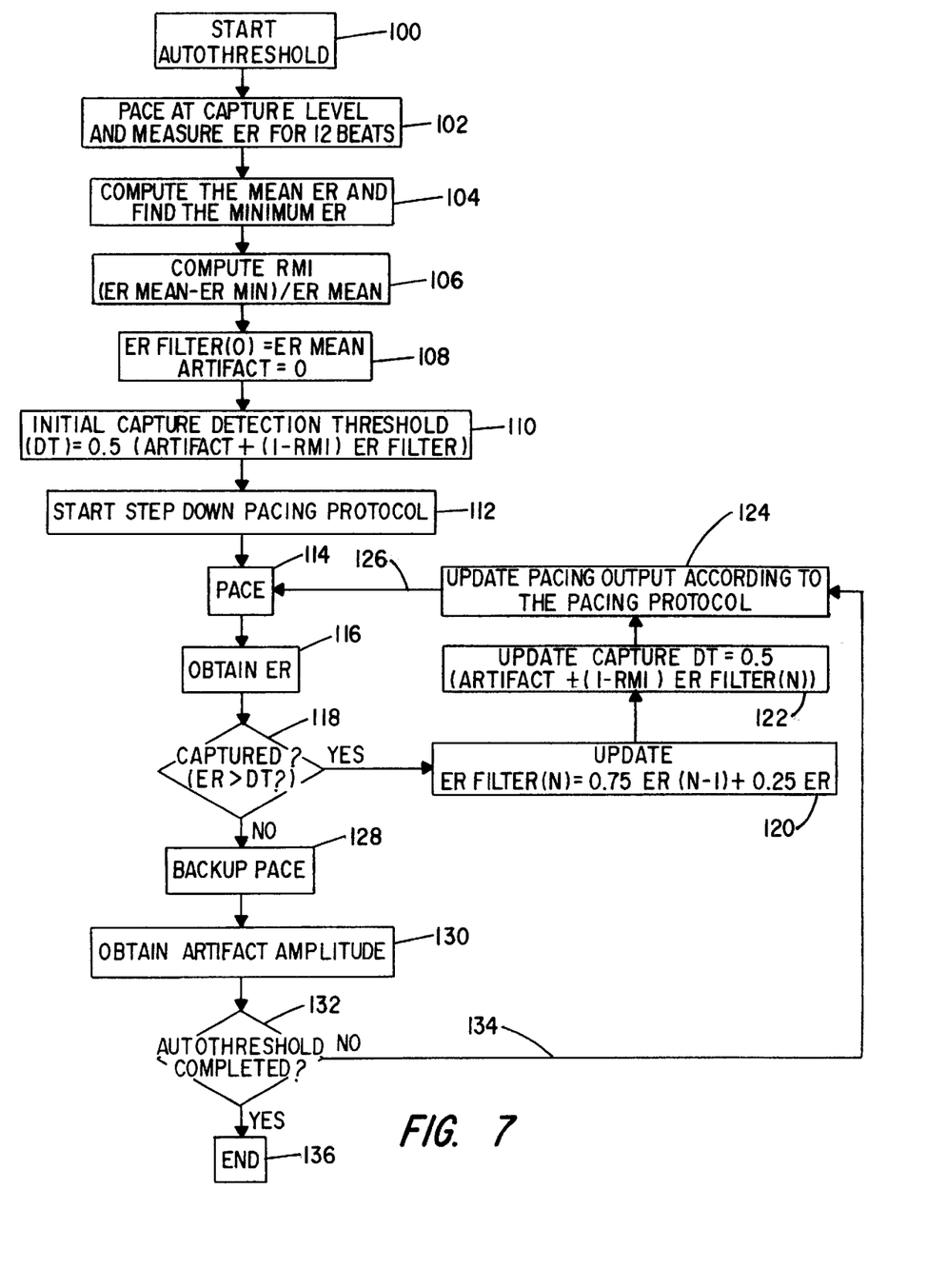
FIG. 7 is a software flow diagram of the automatic adjustment of the evoked response detection threshold algorithm of the present invention.

Without any limitation intended, when an electrocardiogram excursion picked up on lead 14 is signal processed by the sense amplifier/filter circuit 12 and converted to a digital quantity by A/D converter 26, a digital quantity proportional to the excursion is applied to one input of the digital comparator 30 and to the controller 28. If the electrocardiogram excursion exceeds the sensing threshold, the controller processes the signal as a cardiac depolarization, "measuring" the amplitude of the depolarization wave. Once the amplitude measurements have been made for a predetermined number of beats, the controller 28 initiates a sequence to determine and adjust the evoked response detection threshold. FIG. 7 illustrates a method of determining and modulating the evoked response detection threshold in conjunction with the modulating amplitude of evoked response.

Once the automatic evoked response detection threshold determination is initiated (see block 100), the patient's heart is paced at the current capture level for a predetermined number of beats. The maximum amplitude of each evoked response over the predetermined number of beats is measured utilizing the peak detector, comparator and controller as described above in greater detail (see block 102). A value associated with each maximum amplitude may be stored in the memory of the controller. The predetermined number of beats should include at least one complete cycle of the respiration modulation. The mean amplitude and minimum amplitude for all of the maximum amplitudes over the predetermined number of beats is then determined and stored (see block 104). A first constant value referred to as the "Respiration Modulation Index" or RMI is determined according to the following equation:

$$(ER_{mean} - ER_{min})/ER_{mean}$$

wherein $ER_{mean}$ is the mean amplitude for all of the maximum amplitudes over the predetermined number of beats and $ER_{min}$ is the minimum amplitude for all of the maximum amplitudes over the predetermined number of beats (see block 106). A second constant value identified as the $ER_{filter}$ (described below in greater detail) is initially set equal to the determined $ER_{mean}$ and a value corresponding to an amplitude of artifact is initially set equal to zero (see block 108). The evoked response detection threshold (ERDT) is then determined according to the following equation:

$$ERDT = k(\text{Artifact} + ER_{Min})$$

where k is a predefined constant that may range between 0.1 to 0.9 and $ER_{Min}$ is the minimum evoked response due to modulation. The $ER_{Min}$ takes into account both the modulation due to respiration and the modulation due to other factors as follows:

$$ER_{Min} = (1 - RMI)(ER_{Filter})$$

(see block 110). This evoked response detection threshold (ERDT) may be utilized and updated during a capture detection step down pacing protocol (see block 112). A pacing stimulus is delivered and then the rhythm management device senses for an evoked response (see blocks 114 and 116). A determination is then made whether a signal is sensed having an amplitude greater than the ERDT (see decision block 118).

If a maximum amplitude of the sensed signal exceeds the ERDT it is assumed that this signal corresponds to an R-wave and capture is assumed. The value corresponding to the $ER_{Filter}$ is then updated according to the following equation:

$$ER_{Filter(n)} = a(ER_{Filter(n-1)}) + b(ER_n)$$

where n=0 for the initial determination of the $ER_{Filter}$ value and increases by an integer number for each subsequent determination of the ERDT, and "a" and "b" are coefficients wherein $a+b=1$ (see block 120). In the preferred embodiment "a" is set equal to 0.75 and "b" is set equal to 0.25. Those skilled in the art will appreciate that the $ER_{Filter}$ provides a moving average of the evoked response, thereby adapting the evoked response detection threshold to changes in the evoked response amplitude. The ERDT is updated according to the following equation:

$$ERDT_n = 0.5(\text{Artifact} + ((1 - RMI)ER_{Filter(n)}))$$

where the RMI is updated at predetermined intervals, with 21 hours being preferred (see block 122). Without limitation, the pacing output may then be updated according to a known suitable pacing protocol (see block 124). The next pace in the pacing step down protocol may be delivered (see loop 126). If after a pacing stimulus is delivered and the maximum amplitude of the electrocardiogram signal does not exceed the ERDT then a backup pace is delivered (see block 128). The artifact amplitude is then measured from the electrocardiogram signal (see block 130) and it is determined whether the autothreshold protocol is complete. If the protocol is not complete, the pacing output is updated according to known suitable pacing protocol (see loop 134, block 124 and loop 126). In this manner the detection threshold is defined greater than the amplitude for maximum artifact and less than the amplitude of the minimum evoked response.

This invention has been described herein in considerable detail in order to comply with the patent statutes and to provide those skilled in the art with the information needed to apply the novel principles and to construct and use such specialized components as are required. However, it is to be understood that the invention can be carried out by specifically different equipment and devices, and that various modifications, both as to the equipment and operating procedures, can be accomplished without departing from the scope of the invention itself.

What is claimed is:

1. An implantable cardiac rhythm management device capable of automatically detecting an evoked response of a patient's heart and having an adjustable evoked response detection threshold, said device including:

(a) a pulse generator;

(b) a controller for controlling activation of the pulse generator;

(c) a conductor that conducts an electrocardiogram signal, said electrocardiogram signal including electrical impulses corresponding to a cardiac depolarization and noise;

(d) detecting means coupled to the conductor for detecting from the electrocardiogram signal an amplitude associated with an evoked response of the patient's heart, wherein said detecting means includes an adjustable detection threshold;

(e) means for determining a value associated with modulation of the evoked response, wherein said value is determined from the amplitude of a detected evoked response; and (f) adjusting means for adjusting the detection threshold dependent upon the value associated with modulation.

2. The implantable cardiac rhythm management device as recited in claim 1, further including an evoked response filter means for determining an evoked response filter index associated with a maximum amplitude of the detected evoked response for a predetermined number of beats and a maximum amplitude of the detected evoked response for a predetermined number of prior beats.

3. The implantable cardiac rhythm management device as recited in claim 2, further including a respiration modulation means for determining a respiration modulation index from a measured mean of maximum amplitudes of the detected evoked response over a predetermined number of beats and a minimum of maximum amplitudes of the detected evoked response over the predetermined number of beats.

4. The implantable cardiac rhythm management device as recited in claim 3, wherein said value associated with modulation is determined from the respiration modulation index and the evoked response filter index.

5. The implantable cardiac rhythm management device as recited in claim 4, further including a means for determining an amount associated with an artifact baseline of the electrocardiogram signal, and further wherein the detection threshold is set greater than the amount associated with the artifact baseline and less than the minimum of maximum amplitudes of the detected evoked response over the predetermined number of beats.

6. A method for determining an evoked response detection threshold for a cardiac rhythm management device, said method comprising the steps of:
   (a) measuring a maximum amplitude from an electrocardiogram signal corresponding to each evoked response for a predetermined number of heart beats;
   (b) determining the maximum amplitude corresponding to artifact over a predetermined period;
   (c) determining the mean maximum amplitude from the electrocardiogram signal corresponding to each evoked response over the predetermined number of beats;
   (d) determining the minimum maximum amplitude from the electrocardiogram signal corresponding to each evoked response over the predetermined number of beats;
   (e) determining a first value that is a function of the determined mean maximum amplitude and minimum maximum amplitude;
   (f) determining a second value associated with the measured maximum amplitude of the evoked response and an immediately prior measured maximum amplitude for the predetermined number of heart beats; and
   (g) re-setting an evoked response detection threshold as a function of the determined first value, second value, and the maximum amplitude of artifact.

7. The method as recited in claim 6, further including the step of determining the first value once every 21 hours and accordingly re-setting the evoked response detection threshold.

8. The method according to claim 6, wherein if no evoked response is detected, then the evoked response detection threshold is not re-set.

9. The method according to claim 6, wherein if a fusion beat is detected then the evoked response detection threshold is not re-set.

10. The method according to claim 6, wherein the predetermined number of heart beats is set equal to 12.

11. A method of automatically adjusting an evoked response detection threshold in a cardiac rhythm management device corresponding to changes in the amplitude of the evoked response, the cardiac rhythm management device being of the type having means for sensing intrinsic events, a controller, and means controlled by the controller for applying cardiac stimulation to a patient's heart, said method including the steps of:
   (a) setting the detection threshold to a predetermined value;
   (b) sensing electrocardiogram signals having electrical impulses corresponding to cardiac depolarization and noise;
   (c) detecting amplitudes from the sensed signal associated with evoked responses over a predetermined period and determining a value associated with modulation of said amplitudes;
   (d) adjusting the detection threshold dependant upon the determined value associated with modulation.

12. The method as recited in claim 11, further including the step of determining the value associated with modulation once every 21 hours and accordingly adjusting the detection threshold.

13. The method according to claim 11, wherein the detection threshold is not adjusted if an evoked response is not detected.

14. The method according to claim 11, wherein the detection threshold is not adjusted if a fusion beat is detected.

15. The method according to claim 11, wherein the step of determining a value associated with modulation of said amplitudes includes determining an evoked response filter index associated with a maximum amplitude of the detected evoked response for a predetermined number of beats and a maximum amplitude of the detected evoked response for a predetermined number of prior beats.

16. The method according to claim 11, wherein the step of determining a value associated with a modulation of said amplitudes includes determining a respiration modulation index from a measured mean of maximum amplitudes of the detected evoked response over a predetermined number of beats and a minimum of maximum amplitudes of the detected evoked response over the predetermined number of beats.

* * * * *